US005562594A

United States Patent [19]

Weeks

[11] Patent Number: 5,562,594
[45] Date of Patent: Oct. 8, 1996

[54] SHIELDED MINI-APPLICATOR SYSTEM FOR RADIOACTIVE SOURCE TREATMENT OF CANCER OF THE UTERINE CERVIX

[75] Inventor: Kenneth J. Weeks, Chapel Hill, N.C.

[73] Assignee: Duke University, Durham, N.C.

[21] Appl. No.: 257,884

[22] Filed: Jun. 10, 1994

[51] Int. Cl.$^6$ ............................................. A61N 5/00
[52] U.S. Cl. ................................................. 600/3
[58] Field of Search ....................................... 600/1–8

[56] References Cited

U.S. PATENT DOCUMENTS

| | | |
|---|---|---|
| 3,807,386 | 4/1974 | Rocoplan et al. . |
| 4,292,960 | 10/1981 | Paglione .................... 600/6 |
| 4,294,264 | 10/1981 | Fischell et al. ............. 600/6 |
| 5,012,357 | 4/1991 | Schoeppel et al. . |

FOREIGN PATENT DOCUMENTS 1382098  1/1975  United Kingdom ............. 600/8

OTHER PUBLICATIONS

Weeks, K. J., "Brachytherapy Visualization Using AVS," Department of Radiation Oncology, Duke University Medical Center, Durham, NC 27710, presented in May, 1994.

Weeks, K. J., "Superposition of 3D Asymmetric Dose Distributions for Brachytherapy Structures Imaged from Serial CT Slices," submitted to AAPM–CFP for publication in Jun. 1994.

Weeks, K. J. "Measured Dose Distribution for a New Computed Tomography Compatible Tandem–and–Ovoides Applicator System," submitted to AAPM–CFP for publication in Jun., 1994.

Weeks, et al., "A Computed Tomography–Compatible Afterloading Fletcher–Suite–Delclos Colpostat With Adjustable Shielding," *Endocurietherapy/Hyperthermia Oncology*, 5:169–174 (1989).

Nath, et al., "A Dose Computation Model for $^{241}$Am Vaginal Applicators Including the Source-to-Source Shielding Effects," *Med. Phys.*. 17:833–842 (1990).

Weeks, et al., "Dose Calculation and Measurements for a CT Compatible Version of the Fletcher Applicator," *Int. J. Radiation Oncology Biol. Phys.*, 18:1191–1198 (1990).

Weeks, et al., "Design of a Plastic Minicolpostat Applicator With Shields," *Int. J. Radiation Oncol. Biol. Phys.*, 21:1045–1052 (1991).

Nucletron International BV, "Micro Selectron HDR $^{192}$Ir" commercial brochure, Leersum, The Netherlands.

Isotopen–technik Dr. Seuerwein GmBH, "S Gammamed" commercial brochure, Haan/Rheinl, West Germany.

*Primary Examiner*—Angela D. Sykes
*Assistant Examiner*—John P. Lacyk
*Attorney, Agent, or Firm*—Banner & Allegretti, Ltd.

[57] ABSTRACT

This invention provides a novel applicator system for brachytherapy of the uterine cervix which overcomes the problems of the prior art. In particular, this invention provides a Fletcher-like system having an attenuation effect functionally similar to previous applicators, but produced in a smaller sized applicator by a novel arrangement of high and low density metals. The applicator system according to the present invention is constructed so that radiation from the source must transit high density material obliquely to reach the protected tissue, traversing a greater distance in the high density material of the applicator system, with resultant greater attenuation of the radiation for a given amount of high density material. Thus, a far lesser radial extent of highly attenuating material is needed to attain the desired attenuation, and the size of the applicator can be far smaller.

28 Claims, 5 Drawing Sheets

SHIELDED MINI-APPLICATOR SYSTEM FOR RADIOACTIVE SOURCE TREATMENT OF CANCER OF THE UTERINE CERVIX

BACKGROUND OF THE INVENTION

1. Field of the Invention

This invention concerns a method and apparatus for use in treatment of gynecological tumors with radioactive sources, and more particularly, for treatment of cancer of the uterine cervix.

2. Review of Related Art

Brachytherapy is the use of radioactive materials for the purpose of treatment of cancer. It has a 90-year history, dating to within a few years after the discovery of radium by Marie and Pierre Curie in 1898. It has the unique advantage of delivering high doses (energy/mass) of ionizing radiation to small volumes of tissue, combined with a rapid fall off of dose such that distant anatomy is spared. It thus has provided excellent results for localized control of various cancers.

In brachytherapy, the spatial variation of dose (energy absorbed/tissue mass) around each individual source of radiation varies approximately as $1/r^2$, r being the distance from the point of radiation emission to the point of radiation absorption. If more than one radiation source is used, the radiation reaching any particular point is the sum of the radiation emitted from each of the sources. Hence, the dose distribution from a plurality of sources varies anisotropically over the treatment volume.

One of the more successful applications of brachytherapy has been for the treatment of cancer of the uterine cervix. The therapy techniques were developed around sixty years ago with radium and modified with today's usage of cesium-137 and iridium-192. The frequency and severity of complications in treatment of cervical cancer have been correlated with the intracavitary-plus-external-beam dose to the bladder and rectum (Montana, et al., 1989, *Int. J. Radiol. Oncol. Biol. Phys.*, 16:95–100; Perez, et al., 1984, *Cancer,* 54:235–246; Pourquier, et al., 1982, *Int. J. Radiol. Oncol. Biol. Phys.*, 8:1887–1895); Stockbine, et al., 1970, *Am. J. Roentgenol.*, 108:293–304). Analysis and visualization of dose rates in the body is quite complex, and it is essential to avoid cold (lower dose) spots in the tumor and avoid hot (higher dose) spots in the rectum and bladder. The nominal rules for this treatment are based on evaluation of the dose rate at a few points in the patient (Tod, et al., 1938, *Br. J. Radiol.*, 11:809–823).

The Fletcher system (Delclos, et al., 1980, *Int. J. Radiol. Oncol. Biol. Phys.*, 6:1195–1206; Fletcher, 1953, *Radiology,* 60:77–84) provides for tandems of varying curvatures to fit in the uterine cavity in various positions, as well as vaginal colpostats with varying ovoid diameters to fit a range of anatomic variations in the vaginal vault (throughout the following "ovoid" shall refer to the closed end of the colpostat nearest the cervix in which the radioactive source is oriented for treatment after insertion). In the Fletcher system, it is preferable to separate the ovoids as far as possible while maintaining their position as close to the vaginal apex as possible. Once satisfied with the separation, the physician utilizes a locking screw to hold the separation after manual release of the colpostats. The largest possible colpostat diameter is usually employed to improve the tumor-to-normal structure dose ratio, as well as to hinder closure of the ovoids (after manual separation) should the locking screw loosen during the several day treatment.

The Fletcher intracavitary applicator (Fletcher, 1953) was developed following the experience of the Manchester tandem and ovoid system (Tod, et al., 1938) for the treatment of cancer of the uterine cervix using radium sources. The ovoids of the Manchester system are mounted on the ends of the colpostats which have bent handles and are used to separate and position the ovoids. This avoided the problem of directly handling the radioactive source carrying ovoids themselves. The original applicator with preloaded radiation sources was modified by Suit et al. (1963, *Radiology,* 81:126–131) to enable the radiation sources to be afterloaded (inserted into the applicator after it is positioned in the patient), thereby reducing exposure to personnel even further.

Further improvements have been instituted over the years (Delclos, et al., 1980; Delclos, et al., 1978, *Cancer,* 41:970–979; Delclos, et al., 1970, *Radiology,* 96:666–667; Green, et al., 1969, *Am. J. Roentgenol.,* 105:609–613; Haas, et al., 1985, *Int. J. Radiol. Oncol. Biol. Phys.,* 11:1317–1321; Haas, et al., 1980, *Int. J. Radiat. Oncol. Biol. Phys.,* 6:1589–1595; Haas, et al., 1983, *Int. J. Radiol. Oncol. Biol. Phys.,* 9:763–768). The development of minicolpostat applicators, such as the Fletcher-Suit-Delclos (FSD) minicolpostats (MC) (Haas, et al., 1983), was particularly significant. The cross-sectional shape of the ovoids is made in the shape of the letter "D" with the flat side oriented medially and perpendicular to the plane of the cervical os opening to the cervix. This narrows the volume of the applicator which must be pushed up through the vagina. This thereby enables the radioactive source to be positioned closer to the cervix while maintaining the largest possible distance from the source to the lateral vaginal walls. Minicolpostats are useful when the vaginal vault is narrow or distorted due to disease. Experience at the Duke University Medical Center shows that minicolpostats are used in over one-third of the cases. Kuske et al. (1988, *Int. J. Radiat. Oncol. Biol. Phys.*, 14:899–906) has reported a similar frequency of use.

In a effort to ensure that the dose distribution will maximize radiation reaching the tumor tissue and minimize radiation reaching the bladder and rectum, the positioning of the applicator in the patient is always verified using plane radiographic films. Further analysis and/or more precise three-dimensional (3D) information on location can potentially be obtained from computed tomography (CT) or magnetic resonance imaging (MRI). However, a common feature in all the Fletcher designs is the use of high-density metal shields to reduce the dose in the direction of the anterior rectal wall and the bladder trigone (typically 20–30% reduction) without decreasing the dose in the direction of the uterosacral and broad ligaments (Delclos, et al., 1978; Fletcher, 1953). This feature of the prior art applicators precludes the obtaining of these 3D imaging modalities for all patients, because the particular disposition of metals in the conventional applicators leads to reconstruction artifacts, obscuring the imaging of the volumes of interest.

To circumvent this problem, Yu et al. (1982, *Radiology,* 143:536–541) produced a plastic applicator without shields and generated CT images with the applicator in place. Weeks et al. (1989, *Endocuriether. Hyperther. Oncol.*, 5:169–174) have also described a CT-compatible, modified Fletcher applicator system made of plastic with no metal in the applicator (see U.S. Pat. No. 5,012,357). Shields are incorporated in the system of Weeks, et al., 1989, simply by making a container to hold the source and shields together and introducing that container into the applicator after the positioning of the applicator has been verified.

The source+shield container according to U.S. Pat. No. 5,012,357 must then have a much larger diameter than that of just a source carrier. Hence the diameter of the handles of the colpostats must be enlarged to enable the source+shield container to pass through. The handles can no longer be bent without making the handles even larger, but, as the handles get larger it is more difficult to fit the applicator system in patients. Weeks et al. (1991, *Int. J. Radiol. Oncol. Biol. Phys.*, 21:1045–1052) have constructed the smallest possible version of that design, and practical application of that design has established that the applicator can provide treatment for at most 40% of the patient population at Duke Medical Center. However, the considerable amount of operating room time embodied in trying to determine if the applicator will provide an acceptable treatment generally makes such applicators clinically undesirable. Further, it is generally believed that the applicators as described in U.S. Pat. No. 5,012,357 are too large to provide the same level of quality treatment as has been obtained for many years using the metal (steel) FSD design.

New methods of treating cervical cancer have appeared recently. A high activity iridium-192 source (1.5 mm diameter, 5 mm length) is welded on the end of a cable which is motor driven from a protective source housing within a closed end protective plastic sleeve which has been fixed into an applicator inserted in the patient. Because of the high radioactivity of the $^{192}$I source, the treatment lasts only a few minutes and is thus called high dose rate treatment. Applicators for treatment of cervix and vaginal cancer which have copied the FSD shape must be distinct from the low dose rate FSD applicators because of the difficulty of having the source pass by the structure inherently needed to enable the prior art shields stay in place. In short, no shielded applicator exists which could be placed in the patient in the operating room, sustain a standard FSD low dose rate treatment and be followed by a high dose rate boost a day or two later (for the purpose of reducing the overall hospital time that the patient must endure) without putting a different applicator in the patient.

SUMMARY OF THE INVENTION

It is an object of this invention to provide a novel applicator system for brachytherapy of the uterine cervix which overcomes the problems of the prior art. In particular, it is an object of this invention to provide a Fletcher-like system having a functionally similar attenuation effect as previous applicators produced in a smaller applicator by a novel arrangement of high and low density metals.

It is another object of this invention to provide a Fletcher-like system having no reduction in attenuation effect for the smallest colpostat sizes, such as the minicolpostat size as defined below.

It is yet another object of this invention to provide a Fletcher-like system having CT opaque colpostats and tandems but in such a way as to not compromise utility of CT imaging modality.

It is still another object of this invention to provide a Fletcher-like system having minicolpostat size of D-shaped ovoid (namely 12 mm or less width, 29 mm or less height, and 8 mm or less radius of curvature, excluding the direction of the flat side of the "D").

It is yet another object of this invention to provide a Fletcher-like system having no shield pieces in the sense of prior art.

It is a further object of this invention to provide a Fletcher-like system having ability to utilize both the standard low dose rate cesium tube sources and the new high dose rate iridium source without having to remove the applicator from the patient.

It is yet another object of this invention to provide a Fletcher-like system having construction which obviates the need for extraneous dummy inserters to visualize source position in the CT, X-ray, and MRI imaging modalities. These and other objects are met by one or more of the following embodiments.

In one embodiment, this invention provides an apparatus for applying therapeutic radiation emitted from a radiation source to a predetermined region of tissue within a cavity in the body of a living being, the apparatus comprising applicator means for providing an access passageway to the cavity in the body, the applicator means being preferably made of an aluminum alloy or a combination of aluminum and steel or brass, and including at least a hollow head portion surrounding a hollow cavity and a connected hollow handle portion, with an opening in the hollow handle portion of said applicator means; holder means for holding a radiation source and positioning the radiation source in the hollow head portion of the applicator means, the holder means including a holder protective element of high density metal, preferably a tungsten alloy, directly engaging the radiation source, the protective element having a predetermined configuration, and a handle means for facilitating insertion of the holder protective element and the associated radiation source through the opening of the hollow handle portion and into the hollow head portion of the applicator means, such that the radiation source held by the holder means in the hollow head portion of the applicator means emits radiation impinging on the predetermined region of tissue in a predetermined radiation pattern corresponding to the predetermined configuration of the holder protective element. The apparatus may further contain a tandem made of aluminum or an aluminum alloy. In a preferred mode of this embodiment, the apparatus is adapted for a radiation source which is cylindrically shaped and the holder protective element is disposed longitudinally along the radiation source when the radiation source is held by the holder means in the hollow head portion of the applicator means. In another preferred mode of this embodiment, the hollow head portion of the applicator means generally includes a low density metal, but the hollow head portion of the apparatus may also include an applicator protective element which comprises a high density metal.

In another embodiment the invention provides a radiation source carrier for use in applying therapeutic radiation to a predetermined region of tissue, the radiation source carrier comprising a carrier protective element having a predetermined configuration, and retailling means for retaining a radiation source adjacent to the carrier protective element, wherein the carrier protective element directly engages the radiation source such that radiation is emitted by the radiation source in a predetermined radiation pattern corresponding to the predetermined configuration of the carrier protective element, the carrier protective element being preferably disposed longitudinally along a cylindrically shaped radiation source. The carrier protective element is usually made of a high density material, for example a tungsten alloy. In a preferred mode of this embodiment, the carrier protective element includes a partially cylindrical sleeve generally corresponding to the cylindrically shaped radiation source, most preferably including a first end having an accurate opening for inserting the radiation source therein and a second end having a circular end plate for retaining the radiation source within the partial cylindrical sleeve. The retaining means of the radiation source carrier may include a semi-cylindrical clip for holding the radiation source within said partial cylindrical sleeve, the clip and the carrier protective element being preferably made of different metals.

In yet another embodiment, the invention provides a method of applying therapeutic radiation to cervical tissue within the body of a living human, comprising providing applicator means for providing an access passageway to a vaginal cavity in a human body, the applicator means including a hollow head portion adapted for insertion into the vaginal cavity, a hollow handle portion connected to the hollow head portion, and an opening in the hollow handle portion extending to an interior of the hollow head portion, the opening providing access to the interior of the hollow head portion from outside the body of the human when the hollow head portion is inserted into the vaginal cavity, positioning the applicator means in the vaginal cavity of the human such that insertion into the hollow head portion of a radiation source will cause radiation from the radiation source to impinge on a predetermined region of tissue in a predetermined radiation pattern, irradiating the predetermined region of tissue by inserting a radiation source carrier into the applicator means for a predetermined time period, the radiation source carrier including the radiation source, a carrier protective element directly engaging the radiation source, and a handle means for facilitating insertion of the radiation source and associated carrier protective element through the hollow handle portion of the applicator means and into the hollow head portion, such that radiation emitted by the radiation source impinges on the predetermined region of tissue in the predetermined radiation pattern corresponding to the predetermined configuration of the carrier protective element. Preferably, the applicator means and the hollow head means are made of aluminum or an aluminum alloy, and the carrier protective element is made of a tungsten alloy. The radiation source may be either a low intensity radiation source, such as $^{137}$Cs, or a high intensity source, such as $^{192}$Ir.

In a particularly preferred embodiment of the method of this invention, the radiation source is a low intensity source, and, after the predetermined region of tissue has been irradiated by insertion of the low density source, treatment is continued by removing the low intensity radiation source carrier, providing a high intensity radiation source positioning means for facilitating insertion of a high intensity radiation source into the applicator means, the high intensity radiation source positioning means including a high intensity protective element having a predetermined configuration and hollow shaft means for facilitating insertion of the high intensity radiation source through the hollow handle portion of the applicator means, inserting the high intensity radiation source positioning means into the applicator means such that the high intensity protective element of the high intensity radiation source positioning means is positioned in the hollow head portion of the applicator means, and thereafter, inserting the high intensity radiation source into the vaginal cavity of the human through the hollow shaft of the high intensity radiation source positioning means such that the high intensity radiation source is positioned in the hollow head portion of the applicator means and radiation emitted by the high intensity radiation source impinges on the predetermined region of tissue in the predetermined radiation pattern.

It has been discovered-that the radiation dose received by the normal tissues, such as the bladder and rectum, relative to the dose received by tumor tissue, may be reduced by a novel arrangement of high and low density metals in the construction of the applicator system which produces the desired attenuation effect by increasing the attenuation of radiation emitted in the direction of normal tissue; thereby reproducing the functionality of prior art shielding and making possible the solution or correction of numerous deficiencies and limitations of prior art. The applicator system according to the present invention is constructed so that radiation from the source must transit high density material obliquely to reach the protected tissue, traversing a greater distance in the high density material of the applicator system, with resultant greater attenuation of the radiation for a given amount of high density material. Thus, a far lesser radial extent of highly attenuating material is needed to attain the desired attenuation, and the size of the applicator can be far smaller.

BRIEF DESCRIPTION OF THE DRAWINGS

The novel features of the present invention are set out with particularity in the appended claims, but the invention will be understood more fully and clearly from the following detailed description of the invention as set forth in the accompanying drawings, in which:

DETAILED DESCRIPTION OF THE PREFERRED EMBODIMENTS

The intensity of the radiation dose to various tissues in brachytherapy varies inversely with the square of the distance from an emitting point source. This inverse square relationship means that radiation will primarily affect tissue close to the radiation source; tissue far from the radiation source is relatively less affected. Therefore, the purpose of the applicators discussed herein is to position the radiation source as close to tumor tissue as possible and as far from normal tissue as possible. For that purpose, colpostats with smaller ovoids are preferred because they are less sensitive to anatomical variation between patients, thereby offering greater flexibility in positioning the radioactive sources in the patient. This follows from recognition that a smaller ovoid can be easily made bigger (for a given patient) by affixing a plastic cap on the ovoid head. It is equally obvious that the size of the applicator cannot be reduced once it is constructed. The crucial goal is to make the applicator as small as possible to begin with. In one embodiment of the invention, the size of the applicator is made as small as the smallest previously known applicator having the FSD design.

To enhance the selectivity between tumor and normal tissue, the prior art has made use of multiple radiation sources surrounding the tumor, so that the tumor receives radiation emitted from more than one source. Energy absorbed by the tumor is the sum of the energy absorbed from all of the multiple emitting sources, and the total energy absorbed by the tumor will be higher than the amount of energy absorbed by normal tissue, to the extent that normal tissue is adjacent to fewer of the sources. This effect may be further enhanced by placing attenuating material between an emitting radiation source and normal tissue to further attenuate the radiation energy impinging on normal tissue.

The radiation sources used in these procedures are provided as cylinders with relatively uniform radiation emission from all points throughout the source cylinder. $^{137}$Cs sources are usually cylinders approximately three millimeters in diameter and 1.5–2 centimeters long. $^{192}$Ir sources are smaller—usually about 1–1.5 millimeter in diameter and 5 mm long. The Fletcher-Suit and Fletcher-Suit-Delclos (FSD) applicators of the prior art provide a tandem passing through the cervix (to position one or more radiation sources centrally) along with two colpostats to the right and left of the cervix in which radiation sources are positioned. The absence of any radiation sources placed in positions anterior or posterior relative to the cervix means that organs in those directions, particularly the bladder (anterior) and rectum (posterior), receive radiation dose levels that are lower than the amount of radiation reaching the tumor.

The radiation source in the colpostat is preferably positioned with the long axis of the cylinder running generally in an anterior to posterior direction. The cervix is nearly equidistant from multiple points of radiation emission over the length of the radiation source canister positioned in the colpostat, while the normal tissues (bladder and rectum) are much more distant from one of end of the cylinder than the other. As a result, the total integrated radiation dose to the cervix over all the point sources in the source canister is higher than the radiation dose received by normal tissue.

The present invention uses multiple radiation sources, positioned in the manner of the prior art. To further decrease the radiation dose received by the bladder and rectum, FSD colpostats contain shields made of high density metal which further attenuate the radiation emitted in the direction of those organs. In an applicator according to the present invention, protective effect is provided by a novel arrangement of high and low density metals in the construction of the applicator system which produces the desired attenuation effect by increasing the attenuation of radiation emitted in the direction of normal tissue; thereby reproducing the functionality of prior art shielding and making possible the solution or correction of numerous deficiencies and limitations of prior art.

In the traditional FSD applicator, shields resemble sectors of a circular plate of predetermined thickness. The sectors are placed in the applicator so that they will be interposed between the cylindrical $^{137}$Cs source canister and the tissue in need of protection, once the source canister is loaded into the applicator (see FIG. 1). The radiation in the direction of the protected tissue impinges on the shield in a direction generally perpendicular to the circular plate and is attenuated by passage through the shield material. To increase the level of attenuation, the thickness of the plate must be increased. To increase the area of tissue being protected, the radius of the circle must be increased. Thus, to increase the protection offered by the shield, it is necessary to increase the size of the applicator to accommodate a thicker, larger diameter shield. However, the interior anatomy of many women will not accommodate such large applicators, necessitating a compromise between proper positioning of the applicator for effective treatment and adequate attenuation to protect adjacent tissue.

Figure 1:
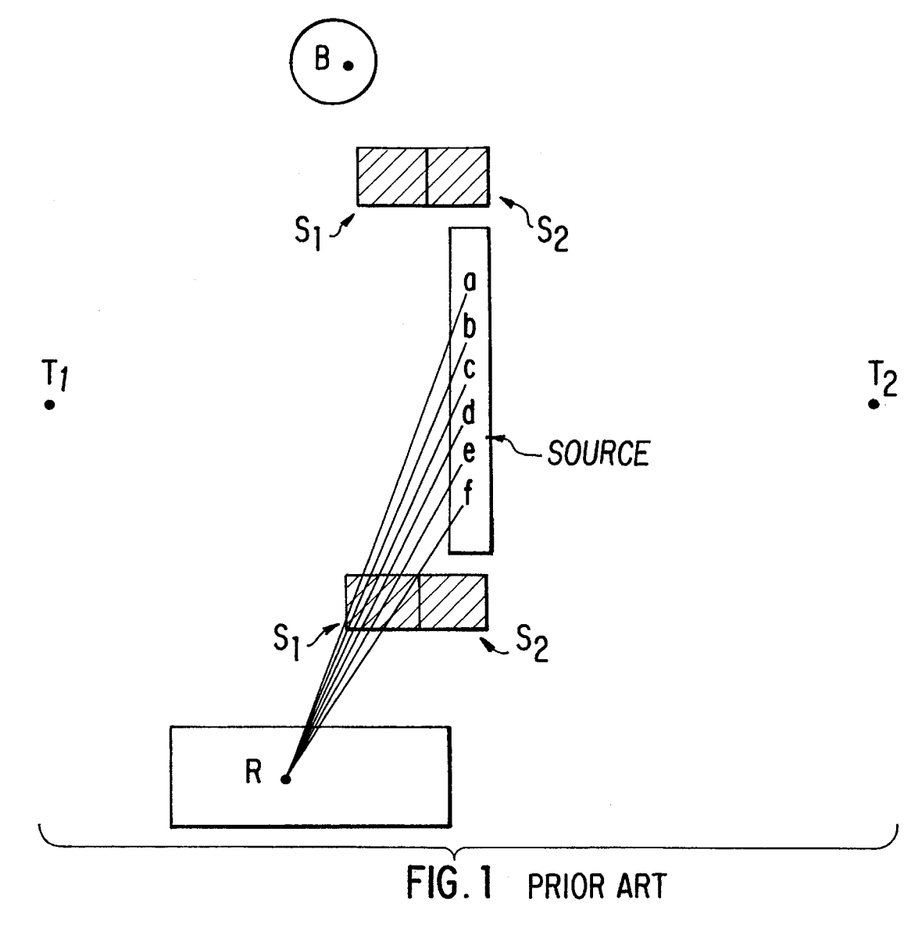
FIG. 1 is a schematic demonstration of the shielding effect according to the prior art.

Prior art in the form of the FSD design splits both the upper and lower shield pieces into two pieces each (see S1 and S2 in FIG. 1 ). The reason for this is that the flat side of the "D" must cut through the space occupied by the shield (as a consequence of the particular 3D arrangement of anatomy relative to the applicator). One part of the upper and lower shields is built into the applicator (namely S2 in FIG. 1). The completing part (S1 in FIG. 1) of those two shields is incorporated into the plastic caps which can be fit over the D shaped ovoid head. In the minimal "D" shaped ovoid head, no cap and hence no shield S1 are present. Thus prior art achieves the smallest D shaped ovoid head at the price of reduced attenuation relative to its own larger diameter ovoid configurations. This invention enables those deficiencies to be avoided and thus enables reduced complication probability for those patients whose anatomy only permits insertion of the smaller size ovoid. Further, newer applicators of even smaller dimensions can be constructed by someone knowledgeable in the art following the teaching herein.

In an attempt to avoid image-destroying CT artifacts caused by the shields in the FSD applicator, modifications of the FSD applicator have been described which allow afterloading of shields along with the radiation source (see U.S. Pat. No. 5,012,357). These modified systems use the same shield material and geometry as the FSD, and they require colpostats with larger ovoids and even larger handles (to accommodate passage of the shields through the handles after the applicator is in place). Prior art in the form of the plastic applicator design with source plus shields in a separate, after-loaded container cannot ever achieve the small width of the D-shape design. Thus, these modified applicators cannot be used in women whose interior anatomy does not accommodate the full-sized FSD applicator.

In contrast, the system of this invention may use a source carrier formed of high density material resembling a segment of a cylinder wall wrapping around the cylindrical source canister and extending beyond the ends of the source canister in anterior and posterior directions (relative to the position of the source canister during therapy). When the applicator according to this invention is positioned in the vagina of a patient and the source carrier according to this invention is loaded into the applicator, the protected tissue will appear at an acute angle to the long axis of the radiation source canister. To reach the protected tissue, radiation from the source must transit the cylindrically-shaped high density material obliquely (see FIG. 2), traversing a greater distance in the high density material with resultant greater attenuation of the radiation for a given amount of high density material. Thus, a far lesser radial extent of highly attenuating material is needed to attain the desired attenuation, and the size of the applicator can be far smaller. Note that in a practical embodiment, the thickness of the cylindrical shell is only 1.3 mm and the shell holds a 3 mm diameter source, thus approximately 6 mm is the restrictive minimum width.

More significantly the length of the ovoid may be decreased. These reductions may be achieved by building more of the high density metal into the colpostat structure. In consequence, the applicator system according to this invention permits the use of substantially attenuated (70% transmission) sources in women who could not accommodate the larger configuration of the FSD applicator or modifications thereof.

Figure 2:
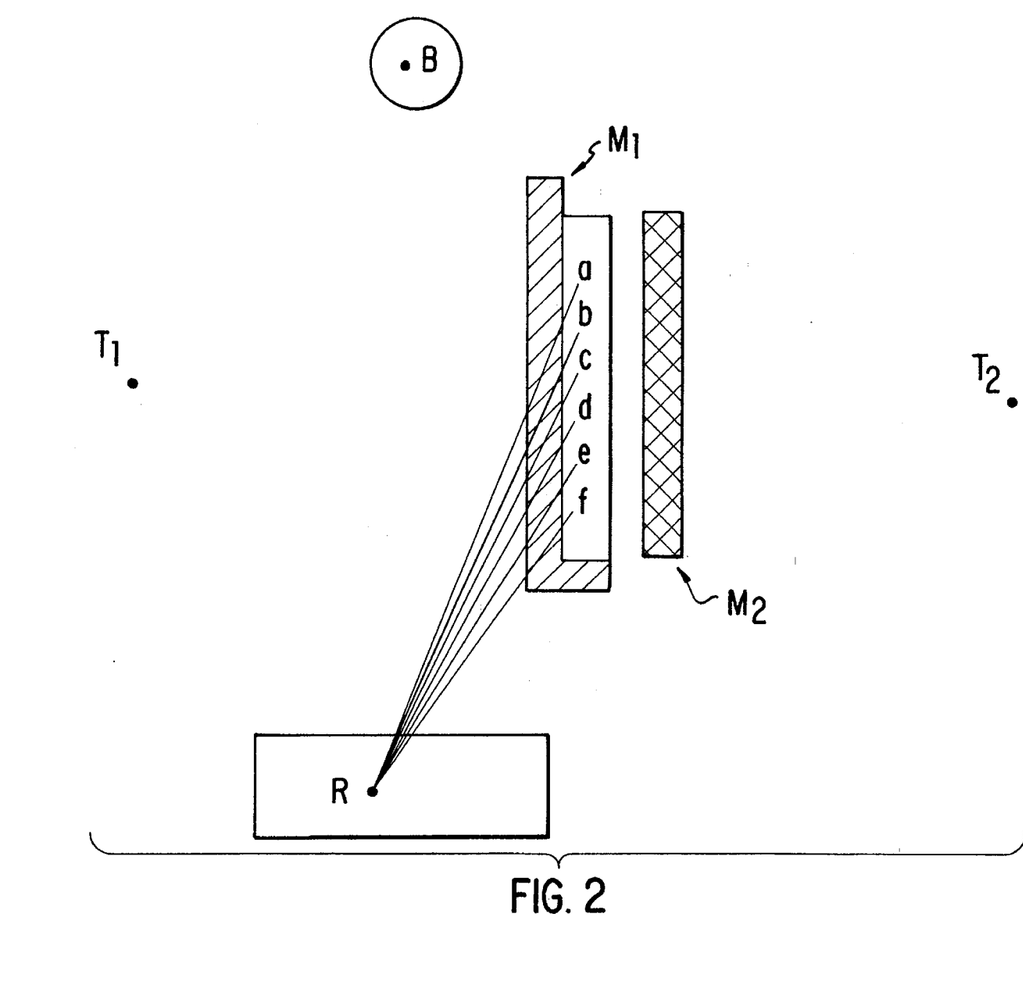
FIG. 2 is a schematic demonstration of the attenuating effect according to the present invention.

Referring to FIGS. 1 and 2, the difference in relative attenuation effect between the present invention and the prior art is schematically demonstrated. FIG. 1 illustrates the positioning of shielding S1 and S2 relative to the radiation source having a large number of point sources a–f emitting radiation. It is clear that there is no differential attenuation from source elements a–f to tumor points T1 and T2. The surrounding steel applicator housing (not shown) reduces the output by 7% roughly equally throughout the volume. The strength of the radiation impinging on the rectum R is attenuated (shown in solid lines) by passage through attenuating material S1 and S2. A similar comparison could be made for bladder point B.

In FIG. 2, the present invention accomplishes the reduction in dose to rectum R by longitudinally aligning a protective element of a high density metal M1 such that longer path lengths of high density material is traversed before radiation impinges rectum R and other vital organs of the body. It may be recognized from FIG. 2 that high density material must be traversed in the path from the source to tumor point T1. This produces some 15% reduction in dose. However, this less desirable effect may optionally be corrected according to this invention by placing another piece of metal (M2 in FIG. 2) on the other side such that the dose to T1 and T2 is close to balanced, and the dose to R and B in FIG. 2 is some 25% to 30% less than the dose to T2 which is the primary tumor direction. The dose to T1 may be, however, reduced relative to T2 also. Thus in a preferred embodiment of the art, an overall 9% reduction in dose (evaluated at points near T2) is produced by the entire metal arrangement and a further 30% reduction in the directions anterior and posterior to the ovoid is produced by the radial close positioning of high density material (M1). In the inferior direction (away from the cervix, i.e. towards T1) an additional 10% or less reduction in dose is present (relative to T2).

To summarize the attenuation effect established by the present invention, the same relative result is achieved as the metal FSD for the critical organs, and tumor bearing structures such as cervix, vaginal fornices, and uterus; however, a different pattern is created inferiorly to the colpostats towards the mid-vaginal walls. This difference is less than 5% due to distance and tandem source superposition which lessens the 10% effect of one source in one colpostat. In short, a new 3D dose distribution is created relative to prior art, which is equivalent in the crucial regions and different in the other regions.

Figure 3:
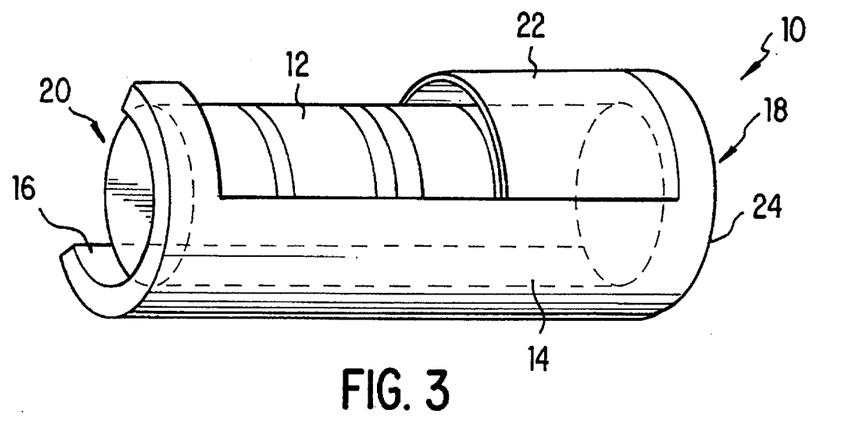
FIG. 3 is an enlarged perspective view of the source carrier of the present invention.

The low density metal (preferably M2=aluminum), though CT opaque, does not compromise identification of structures in the CT scan imaging particularly since it is a low atomic number metal. Alloys of aluminum are all satisfactory as long as the high atomic number components of such alloys are a small percentage of the alloy. Similarly any other low atomic number metals which are approved for therapeutic use in humans may be substituted in the design. Although steel generally produces artifact, it may also be used as long as it is used in thin enough wall sections. At this point it is important to add that metal M2 in FIG. 2 is manifestly built into the applicator housing itself and is radially displaced away from the source by some 3 mm, while metal M1 may be part of the applicator housing or it may be in the source carrier. In one embodiment, M1 may be part of the colpostat. In one embodiment, M1 is the source carrier as shown in FIG. 3. However, there are design advantages to making most of M1 and M2 lie in the applicator itself. These advantages are obvious to one instructed in this art. They permit the applicator system to be reduced in size even further than what has ever been used in prior art. The crucial aspect of the present invention is not how M1 in FIG. 2 is distributed but that it is positioned parallel and most importantly closely adjacent to the source and that the three-dimensional consequences of this positioning are improved or corrected by judicious distribution of metal (M2) in the applicator itself.

High density (e.g., tungsten) metal (M1 in FIG. 2) placement according to this invention preferably extends a distance of about 6 mm on the CT scan. Thus the thickness of 3D space lost via CT image destroying artifact is no more than 6 mm if the tungsten is entirely incorporated in the colpostats, and the artifact is completely absent if the source holder carrier is made of the tungsten as in another embodiment of the invention. In contrast, shields according to the prior art (FSD applicator) would cause a loss of 25 mm of 3D CT space due to artifact from the prior art shields alone. The loss of 3D CT space is actually much larger in practice due to the particular metal steel construction of these applicators.

Prior art applicators for high dose rate afterloaders do not use the FSD shape incorporating shields, since the source cannot pass by the upper shield in the applicator and/or the structure within the applicator which holds the source carrier. The absence of any shields in the conventional sense in an applicator constructed according to the present invention permits, after placement in the patient, either the high or low dose rate or both treatments to be carried out, and both high and low dose rate sources would have attenuation protection for the rectum and bladder. A preferred embodiment of the present invention for use with high dose rate sources would find the tungsten attenuating material partially built into the applicator, namely the lower half. The upper half would help hold and position the source cable mechanism.

I. The Applicator and Radiation Source Carrier

FIG. 3 shows a radiation source carrier or holder 10 according to one embodiment of the invention. Source carrier 10 is itself an attenuating arrangement of high density metal (M1) which functions to control the pattern of emitted radiation from radiation source 12 which is housed within a cylindrical sleeve 16. The attenuation effect depends on the density of the metal material, its atomic number, as well as its geometric arrangement relative to the radioactive source. High density materials are preferred because they provide greater attenuation relative to the volume occupied. For a radiation source containing $^{137}$Cs, a preferred choice for the high density metal attenuating material 14 is a depleted uranium or tungsten alloy and the cylindrical sleeve 16 has a preferred thickness of some 1.3 mm. If lower density materials, such as steel or brass, are used, larger amounts of the material will be needed to achieve the same attenuation effect. Other materials with similar attenuation properties will be readily apparent to the skilled practitioner.

In a preferred embodiment, the high density attenuating holder 10 is augmented by the presence of a clip 22 in stainless steel, preferably attached to the tungsten alloy by epoxy adhesive. On end 18 of the source carrier, the high density material 14 is fashioned into an end plate 24 against which the radiation source canister 12 rests. The opposing end 20 of the sleeve 16 is generally open to receive the radiation source canister 12 therein.

Figure 4:
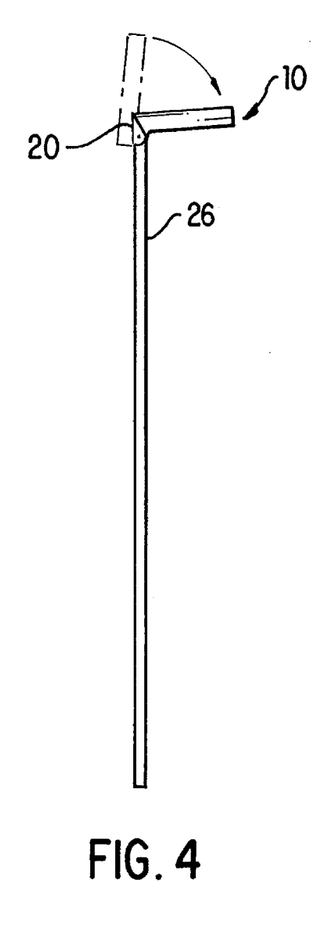
FIG. 4 is a side elevational view thereof.
Figure 5:
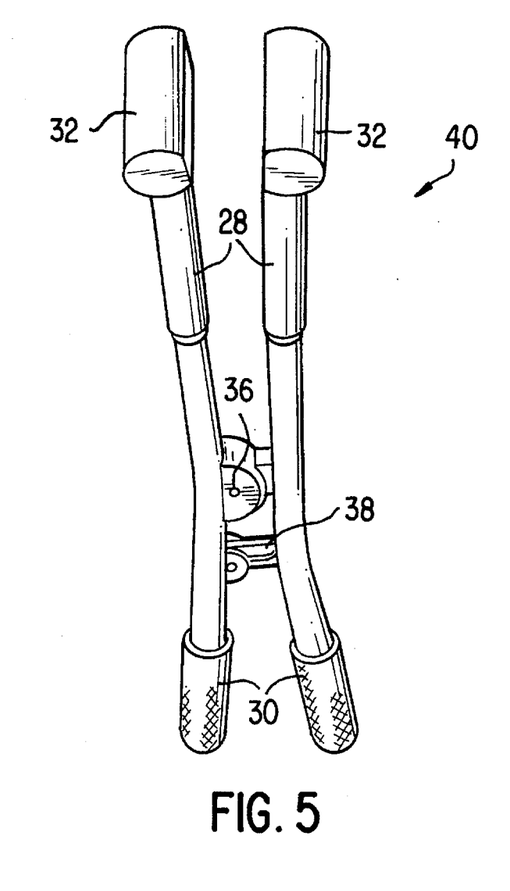
FIG. 5 is a perspective view of an applicator according to the present invention.
Figure 6:
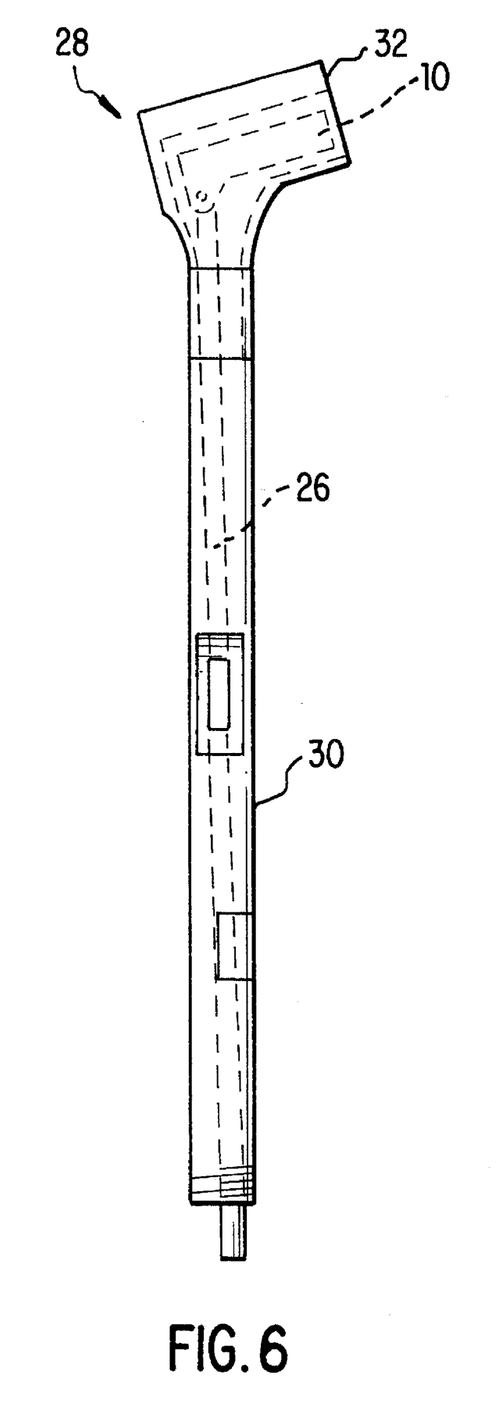
FIG. 6 is a cross-sectional view of a colpostat with the source carrier therein.

Referring also to FIG. 4, in a preferred embodiment of the present invention, a handle 26 is pivotally attached to the open end 20 of the source carrier. The radiation source carrier 10 with source 12 can be inserted into the applicator 40 including colpostats 28, as shown in FIG. 5 and FIG. 6. This handle 26 may be used to push the radiation source carrier 10 (with the radiation source 12 in place) through the hollow colpostat handles 30 and into the hollow D-shaped ovoids or head portions 32. The pivotal attachment allows the radiation source and its carrier to turn once they reach the ovoid 32, and take up the desired position along a generally anterior-to-posterior line. Although the embodiment of FIG. 4 shows handle portion 26 to be a straight rod, the rod is preferably slightly bent to match the bend in the colpostat handles and thereby to facilitate passage of the source carrier 10 through the hollow handle 30 and into the head portion 32.

Figure 7:
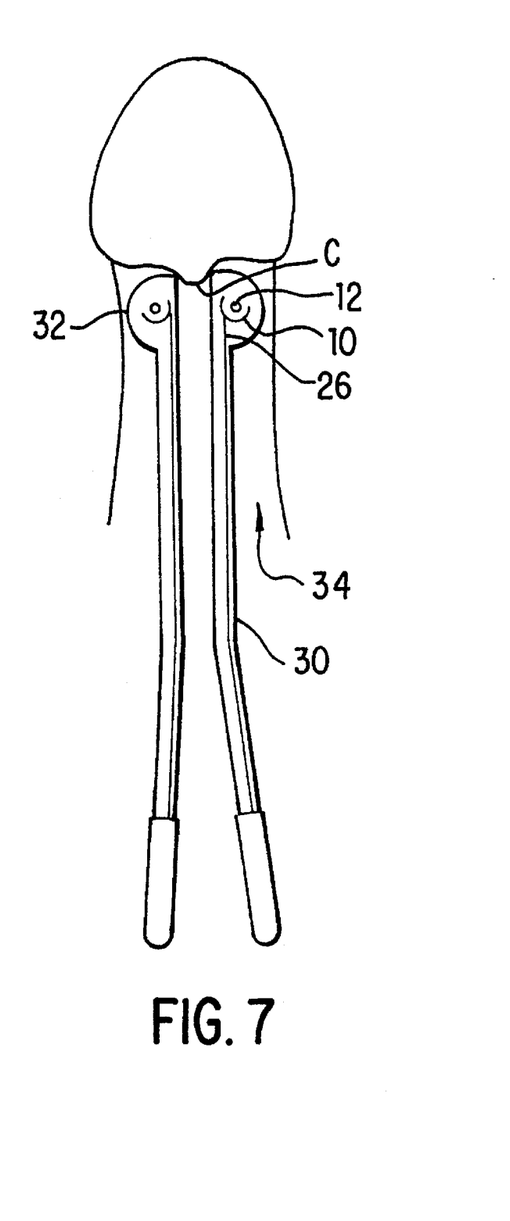
FIG. 7 is a schematic diagram of the colpostats and radiation source carriers of the present invention positioned for therapy in the vagina of a patient.

The colpostat 28 is to be placed during use in a body cavity 34 through an existing portal of the body of a living being (shown schematically in FIG. 7). The specific illustrative embodiment shown herein is intended for placing an irradiation source adjacent to the cervix C of a human being. The applicator 40 comprises a colpostat 28 and a further colpostat 28 which may be joined to one another by pivot joint 36 near the center of each colpostat. It is advantageous to employ two colpostats so as to permit two avenues for introducing irradiation sources within the vaginal cavity on either side of the cervix C.

A specific illustrative embodiment of the present invention described herein provides each of colpostats 28 with respective D-shaped head portions 32. D-shaped head portions 32 are configured fit in the lateral fornices and/or against the cervical portio. The handles 30 of the colpostats are bent to increase leverage for separating the heads of the two ovoids in the patient. In some embodiments, head portions 32 are fitted with auxiliary plastic caps to provide cylindrical shape in order to compensate for anatomical differences between patients. In a practical embodiment, the ovoid portions 32 have a height of approximately 29 mm, a width of the "D" of 12 mm and a radius of curvature (ignoring the flat side of the "D") of 8 mm.

Figure 8A:
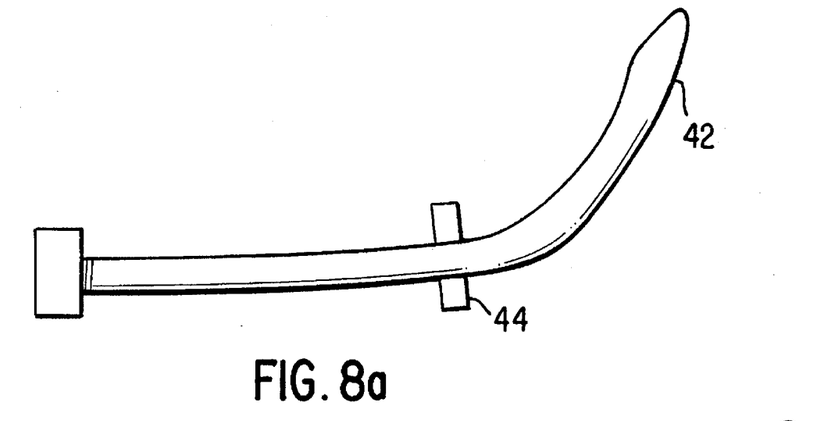
FIGS. 8a–c are schematic diagrams of tandems which may be used as part of the apparatus of this invention.
Figures 8B, 8C:
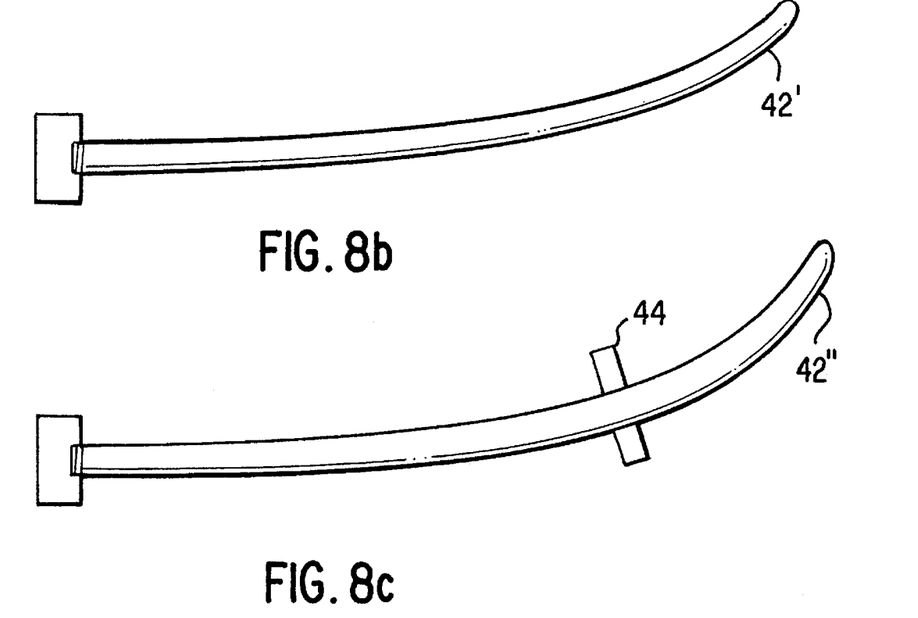

In another preferred embodiment, the applicator is provided with two colpostats 28 as in applicator 40, and an intrauterine tandem is disposed therebetween. As shown in FIG. 8, the tandem 42, 42', 42" may have various configurations. The tandem may float free of the other elements of the applicator 40 arrangement or may be tied or secured to the other components. The tandem is preferably positioned within the body cavity so that a tip portion of the tandem just touches the upper end of the uterus (not shown). In a practical embodiment of the invention, the intrauterine tandem 42, 42', 42" is formed of a CT-opaque material, preferably aluminum, and has an outer diameter of some 6.4 mm. A flange 44 advantageously marks the location of the external cervical os and also prevents the tandem from perforating the uterine wall.

The hollow handle portions 30 of the colpostats 28 are open at the base, permitting insertion therethrough of radiation source carrier. The distal ends of the colpostats are closed by D-shaped head portions 32 which are arranged at predetermined angles with respect to the central longitudinal axes of their respective handle portions. In the specific illustrated embodiment, the angle is approximately 75°. The D-shaped head portions 32 will house the irradiation sources, as will be described herein.

The hollow colpostats may be made of any material which is approved for medical devices to be used in humans, wherein the choice of metals and local concentration of metal is such as to make CT artifact, or MRI artifact, minimal (in geometrical extent) and thus not an impediment to the functionality of the accumulation of anatomical information provided by one or more of these 3-D imaging methods. In particularly preferred embodiments, the colpostat 28 is aluminum, which is directly visualized on CT scans without causing artifacts that obscure the image. Colpostats 28 made of aluminum are also preferred when using magnetic resonance imaging (MRI) to confirm the position of the applicator 40. Steel or brass may be used for part of the colpostat 28, if the construction of the colpostat is such that the total amount of steel or brass in any one CT slice is below the amount which will generate CT artifacts. For example, colpostats in which the hollow handles 30 are made of steel do not generate unacceptable artifacts. On the other hand, steel pivot joint 36 is likely to interfere with CT imaging of that part of the applicator 40. In the case of an applicator which is made for both CT and MRI, all steel must be replaced by aluminum or brass or similar non-magnetic material.

II. Method of Use for Radiation Treatment

The treatment of gynecological tumors, and especially cervical cancer, using low intensity $^{137}$Cs sources begins with the insertion of an applicator, such as applicator 40 and tandem 42, into the patient's vagina in the operating room. This applicator subsequently will hold the cesium source tubes in a definite orientation relative to the cervix and uterus. The patient is then routinely taken only to an X-ray unit to obtain an X-ray image of the applicator to observe positioning. Use of an applicator according to this invention makes possible the use of CT scans for 3D imaging. Typically fifty cross-sectional slices are scanned and in all variations of the applicator contemplated by this invention no more than 2 (or at most 3) of these images would be rendered useless by CT artifact. Metal construction of the applicator according to the present invention allows the applicator to be precisely imaged in the CT scans since it is highly opaque.

In the prior art, accurate positioning by CT imaging required a dummy source carrier, a structural copy of the radiation source carrier made in plastic in which a fake (i.e., dummy) source is inserted, the dummy source being itself made of CT opaque material. (See, e.g., U.S. Pat. No. 5,012,357.) By making a related copy of the radiation source carrier which exactly matches the positioning ability of the fully functional source carrier, the position of the radioactive source in the patient's anatomy could be predicted from CT scans made with the dummy source carrier in place. However, this solution has the associated disadvantage that the positioning determination must be confirmed via additional quality assurance checks throughout the lifetime of the device.

In the present invention, the applicator's opaque image itself allows the source to be localized in the CT scan set, since the position the source will occupy in the applicator is known (i.e., it will be as shown in FIG. 6). In contrast to plastic CT applicators of the prior art, no dummy source inserters are needed with the system of the present invention.

There are three applicator structures: a central tube (tandem 42, 42', 42") which generally will be loaded with no more than four radioactive $^{137}$Cs sources (2.0-cm length, ⅛" diameter) in a longitudinal orientation (parallel to the plane of FIG. 7), and two colpostats 28 (positioned about the cervix on the right and left relative to the patient) holding one radioactive $^{137}$Cs source each in an orientation generally perpendicular to the plane of FIG. 7. The tandem is passed through the vagina and the cervix so that the sources lay in the uterus. The upper ends of the colpostats lay in the vaginal fornices straddling the cervix. The cervix lies just above and between the right and left colpostats, while the uterus surrounds that part of the tandem which lies above the colpostats.

The treatment planning requires that the user decide on the relative strengths (activities) of the radioactive sources such that tumor volume is treated with a therapeutic dose and that structures of tolerance, such as bladder and most importantly rectum, are not damaged. Once this decision is made, the radioactive sources 12 of the appropriate strength are loaded into the applicator 40, carded on their individual radiation source carders 10, and left in place until the tumor tissue has received the intended dose.

The applicator 40 according to this invention has the added advantage of being adaptable for use with high intensity radiation sources, such as $^{192}$Ir sources. Instead of dropping a detached source into the source carrier of FIGS. 3 and 4, a cable-attached iridium source of very small diameter is fed into a flexible plastic sleeve clamped to a smaller diameter version of the apparatus shown in FIG. 3, and the handle function is performed by the flexible plastic sleeve of one meter or so in length (a required part of the high dose rate unit function in which the high dose rate source is required to travel from its housing to the patient). Then the high intensity source is guided by the flexible sleeve through the hollow shaft and into the ovoids, directly adjacent to the high intensity attenuator, which guides the high intensity source into a position where the long axis of the source is generally oriented along a line running in an anterior-to-posterior direction, relative to the patient in whom the colpostat is installed. The attenuator is disposed parallel to the long axis of the high intensity source and extends beyond the anterior and posterior ends of the high intensity source. Radiation from the high intensity source emitted in the direction of the bladder and rectum is attenuated in a manner fully analogous to that observed for the low intensity source (see FIG. 2).

In a particularly preferred embodiment, brachytherapy is performed using both low and high intensity sources in either order, inserted sequentially into the same applicator. In this embodiment, the applicator is positioned in the patient and then the radiation source carrier and low intensity source is inserted for a time less than that necessary to achieve a therapeutic dose. After removal of the radiation source carrier, the high intensity source carrier assembly is inserted into the apparatus, followed by the high intensity source, without the need for repositioning the applicator.

This particularly preferred embodiment provides the advantage of shorter treatment time since a substantial portion of the total dose is supplied by a high intensity source in a short time, rather than by a low intensity source which requires a longer period. A single session in the operating room will suffice to position the colpostats for both sources, and during treatment with both the high and low intensity sources, partial shielding is provided for the bladder and rectum by the disposition of attenuating material according to this invention.

I claim:

1. An apparatus for applying therapeutic radiation emitted from a radiation source to a predetermined region of tissue within a cavity in the body of a living being, said apparatus comprising:

applicator means for providing an access passageway to the cavity in the body, said applicator means including at least a hollow head portion surrounding a hollow cavity and a connected hollow handle portion, with an opening in said hollow handle portion of said applicator means;

holder means for holding a radiation source and positioning the radiation source in said hollow head portion of said applicator means, said holder means including a holder protective element of high density metal adapted to directly engage the radiation source, said protective element having a predetermined configuration, and a handle means for facilitating insertion of said holder protective element and the associated radiation source through said opening of said hollow handle portion and into said hollow head portion of said applicator means, such that the radiation source held by said holder means in the hollow head portion of said applicator means emits radiation impinging on the predetermined region of tissue in a predetermined radiation pattern corresponding to the predetermined configuration of said holder protective element wherein the radiation source is elongated and said holder protective element is disposed longitudinally along the radiation source when the radiation source is held by said holder means in said hollow head portion of said applicator means.

2. The apparatus of claim 1, wherein said applicator means is made of an aluminum alloy or a combination of aluminum and steel or brass.

3. The apparatus of claim 1, wherein said hollow head portion of said applicator means is made of aluminum or an aluminum alloy.

4. The apparatus of claim 1, wherein said applicator means is made of an aluminum portion and a high density metal portion.

5. The apparatus of claim 4, wherein said high density metal is a tungsten alloy.

6. The apparatus of claim 1, wherein said applicator means comprises a first applicator means and said apparatus further including a second applicator means and a tandem made of aluminum or an aluminum alloy disposed between said first and second applicator means.

7. The apparatus of claim 1, wherein said hollow head portion includes an applicator protective element.

8. The apparatus of claim 7, wherein said hollow head portion includes a low density metal.

9. The apparatus of claim 7, wherein said holder protective element and said applicator protective element comprise a high density metal.

10. A radiation source carrier for use in applying therapeutic radiation to a predetermined region of tissue, said radiation source carrier comprising:

a carrier protective element having a predetermined configuration; and retaining means for retaining a radiation source adjacent to said carrier protective element, wherein said carrier protective element is adapted to directly engage the radiation source, the radiation source being elongated and said carrier protective element being disposed longitudinally along the radiation source, such that radiation is emitted by the radiation source in a predetermined radiation pattern corresponding to the predetermined configuration of said carrier protective element.

11. The radiation source carrier of claim 10, wherein said carrier protective element is made of a high density metal.

12. The radiation source carrier of claim 11, wherein said high density metal is a tungsten alloy.

13. The radiation source carrier of claim 11, wherein said carrier protective element includes a partial cylindrical sleeve substantially corresponding to the cylindrically shaped radiation source.

14. The radiation source carrier of claim 11, wherein said carrier protective element further includes a first end having an accurate opening for inserting the radiation source therein and a second end having a circular end plate for retaining the radiation source within said partial cylindrical sleeve.

15. The radiation source carrier of claim 14, wherein said accurate opening is approximately 180 degrees.

16. The radiation source carrier of claim 14, wherein said retaining means includes a semi-cylindrical clip for holding the radiation source within said partial cylindrical sleeve.

17. The radiation source carrier of claim 16, wherein said clip and said carrier protective element are made of different metals.

18. A method of applying therapeutic radiation to cervical tissue within the body of a living human, said method comprising:
   (a) providing applicator means for providing an access passageway to a vaginal cavity in a human body, the applicator means including a hollow head portion adapted for insertion into the vaginal cavity, a hollow handle portion connected to said hollow head portion, and an opening in said hollow handle portion extending to an interior of said hollow head portion, the opening providing access to the interior of said hollow head portion from outside the body of the human when the hollow head portion is inserted into the vaginal cavity;
   (b) positioning said applicator means in the vaginal cavity of the human such that insertion into the hollow head portion of a radiation source will cause radiation from the radiation source to impinge on a predetermined region of tissue in a predetermined radiation pattern;
   (c) irradiating the predetermined region of tissue by inserting a radiation source carrier into said applicator means for a predetermined time period, the radiation source carrier including the radiation source wherein the radiation source is elongated, a carrier protective element, and a handle means for facilitating insertion of the radiation source and associated carrier protective element through the hollow handle portion of the applicator means and into the hollow head portion, such that radiation emitted by the radiation source impinges on the predetermined region of tissue in the predetermined radiation pattern corresponding to the predetermined configuration of the carrier protective element;
   (d) wherein said step of inserting the radiation source carrier further includes aligning the radiation source and the carrier protective element such that the carrier protective element directly engages the radiation source and the carrier protective element is disposed longitudinally along the radiation source when the radiation source is held by the source carrier in the hollow head portion of the applicator means.

19. The method of claim 18, wherein said step of providing applicator means includes providing the applicator means made of aluminum or an aluminum alloy.

20. The method of claim 18, wherein said step of providing applicator means includes providing the hollow head portion of the applicator means made of aluminum or an aluminum alloy.

21. The method of claim 18, wherein said step of irradiating comprises inserting said radiation source carrier means having said carrier protective element made of a tungsten alloy.

22. The method of claim 18, wherein said step of irradiating comprises inserting said radiation source carrier means wherein the radiation source is a low intensity radiation source.

23. The method of claim 22, wherein said step of irradiating comprises inserting said radiation source carrier means wherein the radiation source is a $^{137}$Cs source.

24. The method of claim 18, wherein said step of irradiating comprises inserting said radiation source carrier means wherein the radiation source is a high intensity radiation source.

25. The method of claim 24, said step of irradiating comprises inserting said radiation source carrier means wherein the radiation source is a $^{192}$Ir source.

26. The method of claim 22, further comprising subsequent steps of:
   (d) removing the low intensity radiation source carrier;
   (e) providing a high intensity radiation source positioning means for facilitating insertion of a high intensity radiation source into the applicator means, the high intensity radiation source positioning means including a high intensity protective element having a predetermined configuration and hollow shaft means for facilitating insertion of the high intensity radiation source through the hollow handle portion of the applicator means;
   (f) inserting the high intensity radiation source positioning means into the applicator means such that the high intensity protective element of said high intensity radiation source positioning means is positioned in the hollow head portion of the applicator means; and
   (g) thereafter, inserting the high intensity radiation source into the vaginal cavity of the human through the hollow shaft of the high intensity radiation source positioning means such that the high intensity radiation source is positioned in the hollow head portion of the applicator means and radiation emitted by the high intensity radiation source impinges on the predetermined region of tissue in the predetermined radiation pattern.

27. The method of claim 18 wherein said applicator providing step includes providing an applicator means including a hollow head portion having an applicator protective element.

28. The method of claim 27 wherein said irradiating step further includes emitting radiation in a predetermined radiation pattern formed by the carrier protective element and the applicator protective element; the carrier protective element and the applicator protective element comprising a high density metal.

* * * * *